US012667642B2

(12) United States Patent
Exner et al.

(10) Patent No.: US 12,667,642 B2
(45) Date of Patent: Jun. 30, 2026

(54) TUNABLE, STABLE SCLEROSING FOAM FOR VASCULAR INTERVENTIONS

(71) Applicant: CASE WESTERN RESERVE UNIVERSITY, Cleveland, OH (US)

(72) Inventors: Agata Exner, Westlake, OH (US); Felipe Matias Berg, Cleveland, OH (US); Eric Abenojar, Lakewood, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 243 days.

(21) Appl. No.: 18/518,671

(22) Filed: Nov. 24, 2023

(65) Prior Publication Data

US 2024/0165294 A1 May 23, 2024

Related U.S. Application Data

(60) Provisional application No. 63/384,788, filed on Nov. 23, 2022.

(51) Int. Cl.
*A61L 24/00* (2006.01)

(52) U.S. Cl.
CPC ....... *A61L 24/0036* (2013.01); *A61L 24/0015* (2013.01); *A61L 2300/406* (2013.01); *A61L 2300/442* (2013.01)

(58) Field of Classification Search
CPC ............. A61L 24/0036; A61L 24/0015; A61L 2300/442
See application file for complete search history.

(56) References Cited

U.S. PATENT DOCUMENTS

2005/0002873 A1* 1/2005 Harman ................ A61K 9/124
424/47
2008/0243068 A1* 10/2008 Ramzipoor ........ A61B 17/1214
604/103.05

FOREIGN PATENT DOCUMENTS

EP 1694292 * 8/2006
WO WO 2016/139597 * 9/2016 ............. A61P 35/00

* cited by examiner

*Primary Examiner* — Shirley V Gembeh
(74) *Attorney, Agent, or Firm* — Tarolli, Sundheim, Covell & Tummino LLP

(57) ABSTRACT

A sclerosing foam includes a liquid phase and a gas phase, wherein the liquid phase comprises at least one sclerosing agent and the gas phase comprises at least about 50% by volume of a pefluorocarbon gas.

20 Claims, 13 Drawing Sheets

TUNABLE, STABLE SCLEROSING FOAM FOR VASCULAR INTERVENTIONS

RELATED APPLICATION

This application claims priority from U.S. Provisional Application No. 63/384,788, filed Nov. 23, 2022, the subject matter of which is incorporated herein by reference in its entirety.

BACKGROUND

Vascular anomalies are major diseases that seriously endanger human health, including venous malformations, arteriovenous malformations, hemangioma, lymphatic malformations and the like, among which venous malformations are the most common. Venous malformations can occur in any region of the human body, and about 60% occur in the maxillofacial region. Depending on the location and severity of the disease, on the one hand, the disease can seriously affect the appearance and function of the involved organs, and can be life-threatening due to complications such as infection, bleeding, and respiratory obstruction. On the other hand, the disease often requires life-long treatment, and its social harm is no less than that of malignant tumors.

The current treatment strategy for venous malformations is comprehensive treatment based on sclerotherapy, combined with surgery, laser, interventional therapy, and other methods. The principle of sclerotherapy is to destroy the endothelial cells of the diseased blood/lymphatic vessels with drugs (sclerosing agents) to achieve the purpose of treatment. There are three commonly used sclerosing agents in clinical practice: anhydrous ethanol, polidocanol and bleomycin. Among them, anhydrous ethanol has the strongest sclerosing effect, but has the most serious side effects. In the sclerotherapy process, certain liquid sclerosing agent can be mixed with air to make foam to form a foam sclerosing agent. The latter has more advantages, such as better effect, more safety and fewer side effects than the liquid sclerosing agent, and the advantages are quite significant. Among the above three sclerosing agents, currently only polidocanol can be made into foam, while absolute ethanol and bleomycin cannot directly form foam with air. Polidocanol has a mild effect, although the therapeutic effect is significantly improved after being made into foam, its therapeutic effect is far weaker than that of anhydrous ethanol.

Rare but severe complications can be associated with sclerotherapy, such as pulmonary embolism and stroke. This is caused by air entering the pulmonary or brain arteries. Using a less stable foam in conditions where the risk of embolization is high, although less effective for treating the target lesion presents a safer strategy. On the other hand, in locations where the risk of those complications is low, foams with higher stability can be used to achieve better treatment outcomes.

SUMMARY

Embodiments described herein relate to an embolic or sclerosing foam that includes a sclerosing agent, particularly a sclerosing solution, which can be used in the treatment of various medical conditions involving blood vessels, particularly varicose veins and other disorders involving venous malformation, as well as cancer or solid tumors.

In some embodiments, the sclerosing foam includes a liquid phase and a gas phase. The liquid phase can include at least one sclerosing agent and the gas phase comprises at least about 50% by volume of a perfluorocarbon gas, such as $C_2F_6$, $C_3F_8$, and/or $C_4F_{10}$.

In other embodiments, the gas phase comprises at least about 55%, at least about 60%, at least about 65%, at least about 70%, at least about 75%, at least about 80%, at least about 85%, at least about 90%, at least about 95%, or at least about 99% by volume $C_2F_6$, $C_3F_8$, and/or $C_4F_{10}$. In still other embodiments, the gas phase is free of air.

In some embodiments, the sclerosing agent includes a solution of an anionic surfactant. The anionic surfactant can include at least one of sodium tetradecyl sulfate (STS), polidocanol, ethanolamine oleate, sodium morrhuate, or an analogue thereof. The anionic surfactant may be diluted, for example, with an aqueous carrier, such as water or saline.

In other embodiments, the liquid phase can include an aqueous sodium tetradecyl sulfate solution, such as about 0.3% w/v to about 3% w/v of sodium tetradecyl sulfate (STS) in an aqueous carrier.

In some embodiments, the foam has a liquid to gas ratio of about 1:1.5 to about 1:4.

In other embodiments, the foam can include at least one a radio-opaque agent in an amount effective to enhance radio contrast and/or the stability of the foam.

In some embodiments, the radio-opaque contrast agent includes an oil based iodine contrast agent, such as an ethiodized oil contrast agent. The ethiodized oil contrast agent can include a combination of iodine and ethyl esters of fatty acids of poppyseed oil.

In other embodiments, the foam can include an antibiotic.

In some embodiment, the foam can have a half-life of at least about 10 minutes, at least about 30 minutes, at least about 60 minutes, at least about 90 minutes, at least about 120 minutes, at least about 180 minutes or more.

In other embodiments, at least about 75%, at least about 80%, at least about 85%, at least about 90%, or at least about 99% of bubbles of the foam have a diameter less than about 200 μm, less than about 175 μm, or less than about 150 μm, for example about 10 μm to about 100 μm upon production and have a diameter that remains consistently smaller than about 200 μm after about 30 minutes.

DETAILED DESCRIPTION

Figures 1, 2:
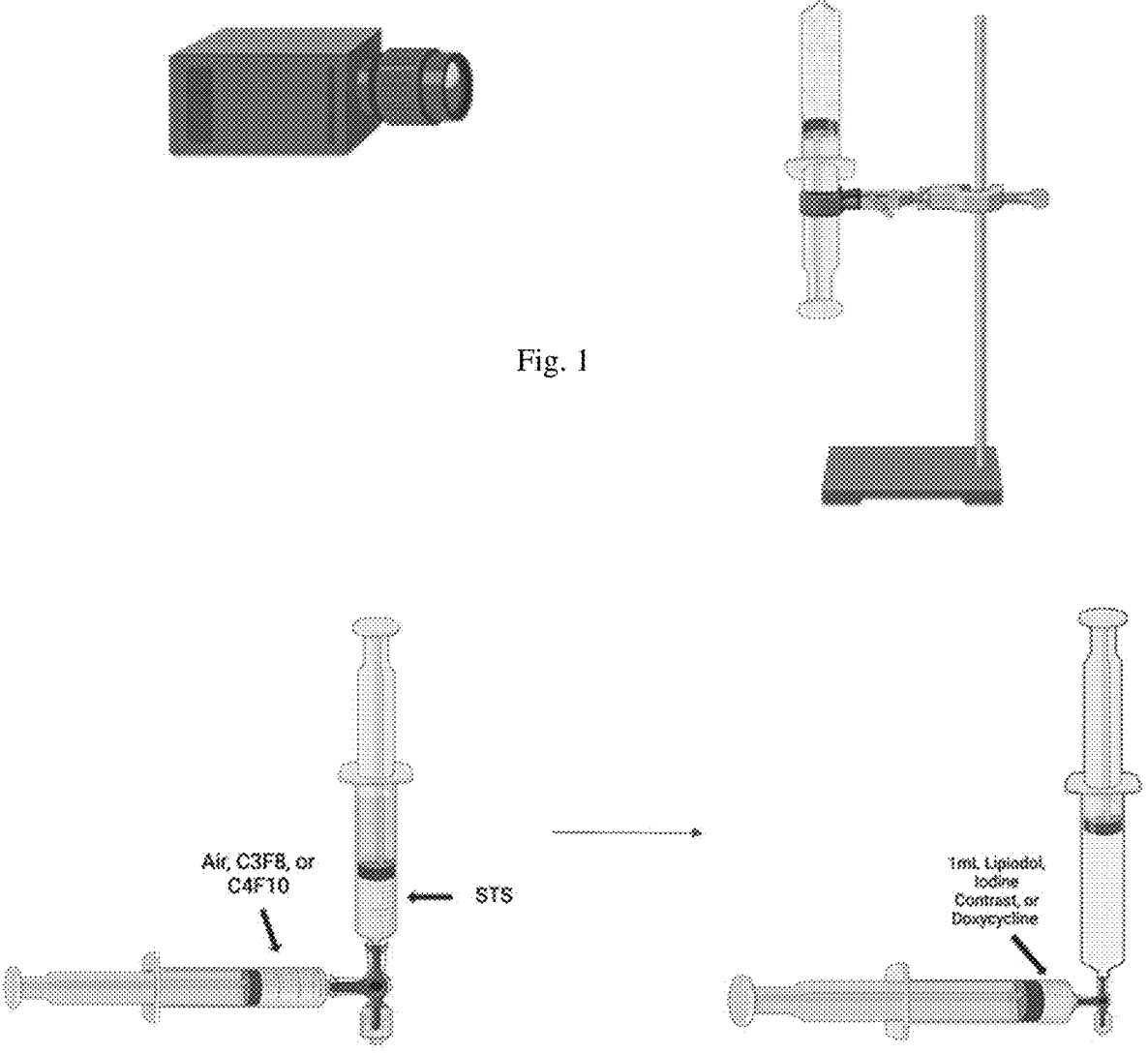
FIG. 1 illustrates a schematic representation of a method of measuring foam decay.
FIG. 2 illustrates a schematic representation of an apparatus used to produced a sclerosing foam in accordance with an embodiment.

Embodiments described herein relate to an embolic or sclerosing foam that includes a liquid sclerosing agent, particularly a sclerosing solution, which can be used in the treatment of various medical conditions involving blood vessels, particularly varicose veins and other disorders involving venous malformation, as well as cancer or solid tumors. The sclerosing foam includes a liquid phase and a gas phase. The liquid phase can include at least one sclerosing agent and the gas phase can include at least about 50% by volume of a perfluorocarbon gas, such as $C_2F_6$, $C_3F_8$, and/or $C_4F_{10}$. Advantageously, a sclerosing foam that includes a sclerosing agent and perfluorocarbon gas has enhanced stability and smaller bubble size compared to similar sclerosing foams formed using a sclerosing agent and air. For example, at least about 75%, at least about 80%, at least about 85%, at least about 90%, or at least about 99% of bubbles of the foam have a diameter less than about 200 µm, less than about 175 µm, or less than about 150 µm, for example about 10 µm to about 100 µm upon production and have a diameter that remains consistently smaller than about 200 µm after about 30 minutes. The stability of the sclerosing foam described herein can be adjusted by adjusting the ratio of liquid phase to gas phase, the percentage of perfluorocarbon in the gas phase, the molecular weight of the perfluorocarbon, as well as adding contrast agents to the sclerosing foam to produce foams with tunable stability from minutes to days.

In some embodiments, the gas phase comprises at least about 55%, at least about 60%, at least about 65%, at least about 70%, at least about 75%, at least about 80%, at least about 85%, at least about 90%, at least about 95%, or at least about 99% by volume of a perfluorocarbon gas, such as $C_2F_6$, $C_3F_8$, and/or $C_4F_{10}$.

In still other embodiments, the gas phase includes less than about 50%, less than about 45%, less than about 40%, less than about 35%, less than about 30%, less than about 25%, less than about 20%, less than about 15%, less than about 10%, less than about 5%, less than about 1% by volume $N_2$, $O_2$, $CO_2$, and/or air. In some embodiments, the gas phase is free of $N_2$, $O_2$, $CO_2$, and/or air.

In some embodiments, the liquid phase includes a liquid sclerosing agent. The liquid sclerosing agent can include an aqueous solution of an anionic surfactant, such as a solution of an anionic surfactant and an aqueous carrier, such as water or saline. The anionic surfactant can include at least one of sodium tetradecyl sulfate, polidocanol, ethanolamine oleate, sodium morrhuate, or an analogue thereof.

In other embodiments, the liquid sclerosing agent can include about 0.1% v/v to about 5% w/v about 0.3% w/v to about 3% w/v of sodium tetradecyl sulfate in an aqueous carrier, such as sterile water or physiologically acceptable saline, e.g., about 0.3% w/v to about 3% w/v. The water or saline can also include a physiologically acceptable alcohol, such as ethanol or benzyl alcohol. The saline may be buffered. Some buffered saline can be phosphate buffered saline. The pH of the buffer may be adjusted to be physiological, e.g., from pH about 6.0 to about 8.0, or pH about 7.0 to about 8.0.

For example, the liquid sclerosing agent can include 1 w/v to about 3% w/v SOTRADECOL (Mylan Institutional LLC, Rockford IL). SOTRADECOL is a sterile nonpyrogenic solution for intravenous use as a sclerosing agent. Each mL of 1% (10 mg/mL) SOTRADECOL includes 10 mg of sodium tetradecyl sulfate, 0.02 mL of benzyl alcohol and 4.0 mg of dibasic sodium phosphate, anhydrous in water for injection. 1% SOTRADECOL has a pH 7.9, which can be adjusted with the addition of monobasic sodium phosphate and/or sodium hydroxide added, if needed. Each mL of 3% (10 mg/mL) SOTRADECOL includes 30 mg of sodium tetradecyl sulfate, 0.02 mL of benzyl alcohol, and 9.0 mg of dibasic sodium phosphate, anhydrous in water for Injection. 3% SOTRADECOL has a pH 7.9, which can be adjusted with the addition of monobasic sodium phosphate and/or sodium hydroxide added, if needed.

The liquid phase may additionally include at least one a radio-opaque agent in an amount effective to enhance radio contrast and/or the stability of the foam. In some embodiments, the radio-opaque contrast agent includes an oil based iodine contrast agent such as an ethiodized oil contrast agent. The ethiodized oil contrast agent can include a combination of iodine and ethyl esters of fatty acids of poppyseed oil. The ethiodized oil contrast agent can include, for example, LIPIODOL, (Guerbet, Villepinte, France). Other iodine contrast agents, such as OMNIPAQUE (Marlborough, United States) (5-(Acetylamino)-N,N'-bis(2,3-dihydroxypropyl)-2,4,6-triiodo-1,3-benzenedicarboxamide) can also be used to enhance the contrast of sclerosing foam. Advantageously, LIPIODOL, an ethiodized oil when included in the liquid phase, at amounts of about 1% to about 50%, about 5% to about 40%, about 10% to about 35%, or about 15% to about 33% by volume of the liquid phase can enhance the stability of the sclerosing foam, whereas OMNI-PAQUE had a similar but milder effect. This suggests that non-oil based iodine contrast agents, such as OMNIPAQUE, can be used to enhance contrast of the sclerosing foam without substantially changing its properties, whereas oil based iodine contrast agents, such as LIPIODOL, can provide contrast and enhance stability.

The liquid phase may further contain one or more additional components, such as an antibiotic, e.g., doxycycline, stabilizing agents or foam stabilizing agents, such as glycerol, and alcohols, such as ethanol or benzyl alcohol.

In some embodiments, the foam has a liquid to gas ratio about 1:0.5 to about 1:6, or about 1:1 to about 1:5, or about 1:1.5 to about 1:4. Advantageously, we found that increasing the ratio of the gas phase relative liquid phase can increase the stability of the sclerosing foam.

In some embodiment, the sclerosing foam can have a half-life of at least about 10 minutes. As illustrated in FIG. 1, the half-life can conveniently be measured by filling a syringe with a known volume and weight of the sclerosing foam and allowing the sclerosing foam to decay in a given time allowing calculation of half-life, i.e., conversion of foam back into its component liquid and gas phases. This is preferably carried out at standard temperature and pressure, but in practice ambient clinic or laboratory conditions will suffice. The sclerosing foam including the perfluorocarbon gas and optional iodine contrast agent can have a half-life substantially longer than sclerosing foams that include an air gas phase, for example, a half-life of at least about 30 minutes, at least about 60 minutes, at least about 90 minutes, at least about 120 minutes, at least about 180 minutes or more.

The sclerosing foam can also have a much smaller and more uniform bubble size than sclerosing foams that include air as the gas phase. For example, at least about 50%, at least about 75%, or at least about 90% of bubbles of a sclerosing foam that includes a perfluorocarbon gas can have a diameter less than about 10 mm, less than about 1 mm, or less than about 500 µm.

FIG. 2 is a schematic illustration of a method used to produce an injectable sclerosing foam as described herein. The injectable sclerosing foam can be produced by providing a first syringe containing the perfluorocarbon gas and optional additional gas and a second syringe containing the liquid sclerosing agent and passing the gas and the sclerosing agent back and forth between the first syringe and the second syringe by operation of the first syringe and the second syringe so that the gas and the liquid sclerosing agent mix turbulently to form the foam. Foams arise in the presence of a gas, a foaming liquid sclerosing agent, and turbulence. Turbulence will naturally arise as a consequence of the back-and-forth motion between the syringes.

The method includes a preliminary step of at least partially filling the first syringe with the gas. The gas may be sterilized before or after the first syringe is at least partially filled. Sterilization may be brought about, for example, by exposure to T-radiation.

The first and second syringes are attached to a valve that is selectively adjustable between a first position in which the first and second syringes are not in communication with each other and a second position in which the first and second syringes are in communication with each other. This provides a convenient means to keep the gas and the liquid sclerosing agent separate, by keeping the valve in the first position, until it is desired to mix them, when the valve may be adjusted to the second position. The valve may be a three-port valve. The valve can be attached to the first syringe prior to attachment of the second syringe. Preferably, the valve retains in the first syringe the gas contained in the first syringe. The second syringe can be at least partially filled when the valve is in the first position. The second syringe may be at least partially filled through a nozzle with which it is in communication when the valve is in the first position. Preferably the nozzle is attached to a needle.

Alternatively, the method may include a preliminary step of at least partially filling the second syringe with the liquid sclerosing agent and the optional radio-opaque agent.

When the foam has been produced, it may be withdrawn into either syringe and the syringe containing the sclerosing foam may then be detached from the valve. A needle may then be connected to the syringe so that it is ready for use in an injection. The sclerosing foam is thus produced in a syringe that may be used directly, without the need to transfer it to another container, a transfer that might result in deterioration and/or contamination of the sclerosing foam.

Excess sclerosing foam may be retained in one syringe after the other syringe is detached. It is thus retained in a sterile environment and is ready for use at a later time. The back and forth transfers may need to be repeated to return the foam to a useable state.

The method may further comprise the step of adjusting the valve to a third position in which the first syringe and the second syringe are in reduced communication compared with the second position. Reducing the communication between the syringes can in some instances provide a foam having smaller bubbles and a longer life. The valve may comprise a collar member defining at least two apertures and a valve member defining a bore and communication between the first and second syringes may be reduced by rotation of the collar member so that the apertures and bore are misaligned relative to each other. Communication may be progressively reduced further by adjusting the valve to a number of further positions.

Figure 3:
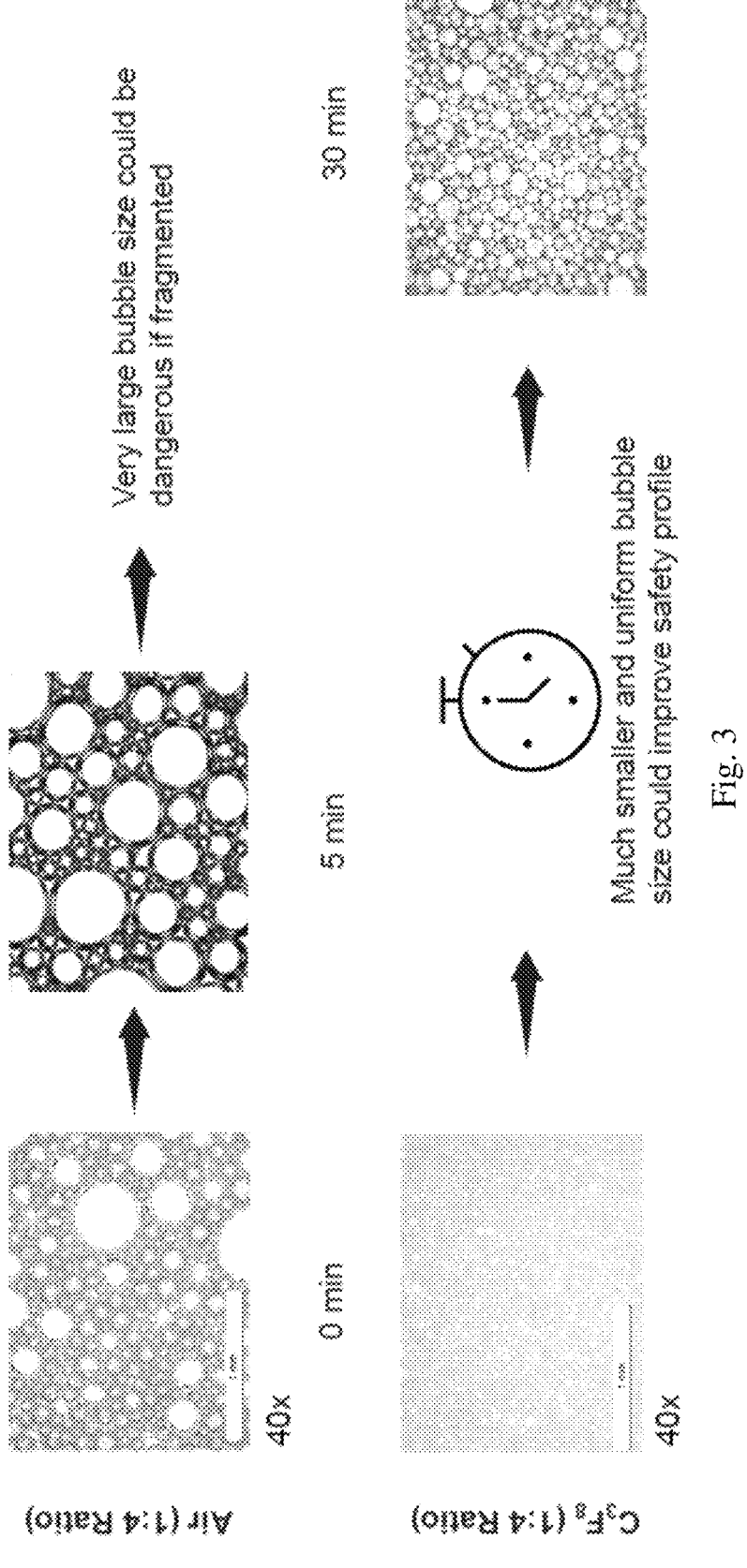
FIG. 3 are images of foams produced at an STS:air ratio of 1:4 and STS:$C_3F_8$ ratio of 1:4 upon production and after 5 minutes and 30 minutes, respectively.

The gas and liquid sclerosing agent can be passed back and forth at least about 5 times, at least about 10 times, at least about 15 times, at least about 20 times, at least about 30 times, at least about 40 times, or more. Preferably, the gas and liquid sclerosing agent are passed back and forth at least 20 times. Advantageously, the perfluorocarbon gas and liquid sclerosing agent are passed back and forth a number of times effective to form a sclerosing foam where at least about 75%, at least about 80%, at least about 85%, at least about 90%, or at least about 99% of bubbles of the foam have a diameter less than about 200 µm, less than about 175 µm, or less than about 150 µm, for example about 10 µm to about 100 µm upon production and have a diameter that remains consistently smaller than about 200 µm after about 30 minutes (FIG. 3).

In some embodiments, the capacities of the first and second syringes are in the range of about 1 ml to about 20 ml. More preferably, the capacities are in the range about 2 ml to about 5 ml.

The ratio of the volume of liquid sclerosing agent to gas is about 1:0.5 to about 1:6, or about 1:1 to about 1:5, or about 1:1.5 to about 1:4. Preferably, the ratio of the volume of sclerosing liquid to gas is about 1:3 to about 1:5.

The concentration of the sclerosant or anionic surfactant is in the range 0.1% to 5% by weight. Concentrations of STS in the range 1% to 3% by w/v have been found to be suitable in producing foam for treatment of saphenous and recurrent varicose veins. Concentrations of STS in the range 0.3% to 1% by w/v have been found to be suitable in producing foam suitable for treatment of collateral varicose veins.

The dose of the liquid sclerosing agent in the second syringe is in the range 0.25 ml to 4 ml. Doses depend on length and caliber or width of veins to be treated with the foam produced by the method. Doses of foam in the range 1 ml to 10 ml have been found to be suitable in producing foam for treatment of saphenous and recurrent varicose veins as well as collateral varicose veins.

It is a particular advantage that the foam persists for sufficiently long that it can be injected and have effect but it does not persist for too long in the body.

The sclerosing foam produced by the method described herein is suitable for use in methods of treatment of, for example, long and short saphenous veins, recurrent varices and collaterals, reticular varices, telangiectasias, varicocele recurrences or perforator incompetence. A sclerosing foam produced by the method described herein may have other uses in medicine. It may be suitable for use in methods relating to, for example, phlebology, esophageal varices, proctology or angiology.

Other embodiments described herein relate to a method of treating varicose veins by injection with an effective amount of sclerosing foam produced by: providing a first syringe containing a gas including at least 50% by volume perfluorocarbon gas; providing a second syringe containing a liquid sclerosing agent comprising an aqueous solution of an anionic surfactant, such as STS, and optionally a radio-opaque agent; and passing the gas and the sclerosing liquid back and forth between the first syringe and the second syringe so that the gas and the sclerosing liquid mix turbulently to form the foam.

Still other embodiments relate to a method of treating esophageal varices by injection with an effective amount of sclerosing foam produced by: providing a first syringe containing a gas including at least 50% by volume perfluorocarbon gas; providing a second syringe containing a liquid sclerosing agent comprising an aqueous solution of an anionic surfactant, such as STS, and optionally a radio-opaque agent, and passing the gas and the liquid back and forth between the first syringe and the second syringe by operation of the first syringe and the second syringe so that the gas and the liquid mix turbulently to form the foam.

Other embodiments described herein relate to a method of treating hemorrhoids by injection with an effective amount of sclerosing foam produced by: providing a first syringe containing a gas including at least 50% by volume perfluorocarbon gas; providing a second syringe containing a liquid sclerosing agent comprising an aqueous solution of an anionic surfactant, such as STS, and optionally a radio-opaque agent, and passing the gas and the liquid back and forth between the first syringe and the second syringe by operation of the first syringe and the second syringe so that the gas and the liquid mix turbulently to form the foam.

Other embodiments described herein relate to a method of treating varicocele by injection with an effective amount of sclerosing foam produced by: providing a first syringe containing a gas including at least 50% by volume perfluorocarbon gas; providing a second syringe containing a liquid sclerosing agent comprising an aqueous solution of an anionic surfactant, such as STS, and optionally a radio-opaque agent, and passing the gas and the liquid back and forth between the first syringe and the second syringe by operation of the first syringe and the second syringe so that the gas and the liquid mix turbulently to form the foam.

Still other embodiments described herein relate to a method of treating cancer by injection with an effective amount of sclerosing foam produced by: providing a first syringe containing a gas including at least 50% by volume perfluorocarbon gas; providing a second syringe containing a liquid sclerosing agent comprising an aqueous solution of an anionic surfactant, such as STS, and optionally a radio-opaque agent, and passing the gas and the liquid back and forth between the first syringe and the second syringe by operation of the first syringe and the second syringe so that the gas and the liquid mix turbulently to form the foam. The sclerosing foam can be used to destroy the tumor vascular supply or simply locally injected directly into the tumor to cause necrosis.

In some embodiments, the liquid sclerosing agent can be combined with a chemotherapeutic or anti-cancer agent such that a chemoembolization foam is produced. The chemoembolization foam can have two therapeutic purposes, the occlusion of vasculature supplying blood to the tumor via the embolization effect (tumor necrosis), and the delivery of an anti-cancer agent or chemotherapeutic into the tumor via elution of the anti-cancer agent or chemotherapeutic from the foam. The combination of embolization and drug delivery, or chemoembolization, has been found to be superior to the treatment of cancer as compared with embolization alone.

Advantageously, the sclerosing foam described herein is echogenic, which allows it to be used in methods of treatment with co-use of ultrasound, such as duplex guiding, and in diagnosis by ultrasound.

Still other embodiments described herein relate to a kit comprising a first syringe, a second syringe and a valve to which the first and second syringes may be attached and which is selectively adjustable between a first position, in which the first and second syringes are not in communication with each other, and a second position, in which the first and second syringes would be in communication with each other if they were attached to the valve.

In the kit the valve is attached to the first syringe and is in the first position and the first syringe contains a sterilized gas at least 50% by volume perfluorocarbon gas. If desired, the kit further comprises a liquid sclerosing agent, contained, for example, in the second syringe. The liquid sclerosing agent can include an aqueous solution of anionic surfactant, such as STS, and optionally a radio-opaque agent.

According to another embodiment, there is provided an injectable sclerosing foam produced by: drawing a gas including at least 50% by volume perfluorocarbon gas into a first syringe; drawing a sclerosing liquid including an aqueous solution of anionic surfactant, such as STS, and optionally a radio-opaque agent into a second syringe; and passing the gas and the sclerosing liquid back and forth between the first syringe and the second syringe by operation of the first syringe and the second syringe so that the gas and the liquid mix turbulently to form the foam.

The following example is for the purpose of illustration only and is not intended to limit the scope of the claims, which are appended hereto.

Example 1

Influence of LIPIODOL and Iodine Contrast on Sclerosing STS Foam Stability

Sclerotherapy is a cornerstone treatment for various venous diseases, notably varicose veins and arterio-venous malformations. Understanding the impact of commonly added contrast agents, such as LIPIODOL and iodine contrast, OMNIPAQUE, on sclerosing foam performance, is vital for selecting the appropriate formulations in clinical practice. This Example describes how the inclusion of iodinated contrast media influences the stability of sclerosing foam formulations routinely employed in patient care.

Materials and Methods

Foams were generated using two 10 mL syringes connected by a 3-way stopcock. One syringe was filled with room air, while the other contained 2 mL of sodium tetradecyl-sulfate (STS). The components were mixed through the stopcock 30 times (Tessari's method). For contrast-bearing formulations, 1 mL of LIPIODOL (Guerbet, Villepinte, France) or OMNIPAQUE (Marlborough, United States) were added to the mixture (2 mL of STS+1 mL of contrast). Each trial set encompassed ratios of 1:1.5, 2, 3, and 4 mL of STS to room air. Foam decay was monitored using a 4K camera over 1 hour, followed by hourly snapshots for 3 hours. Supplementary images were captured at the 24-hour mark if any foam persisted. Decay of foam was calculated using the formula (foam left in syringe)/(total volume).

Results

Figure 5A:
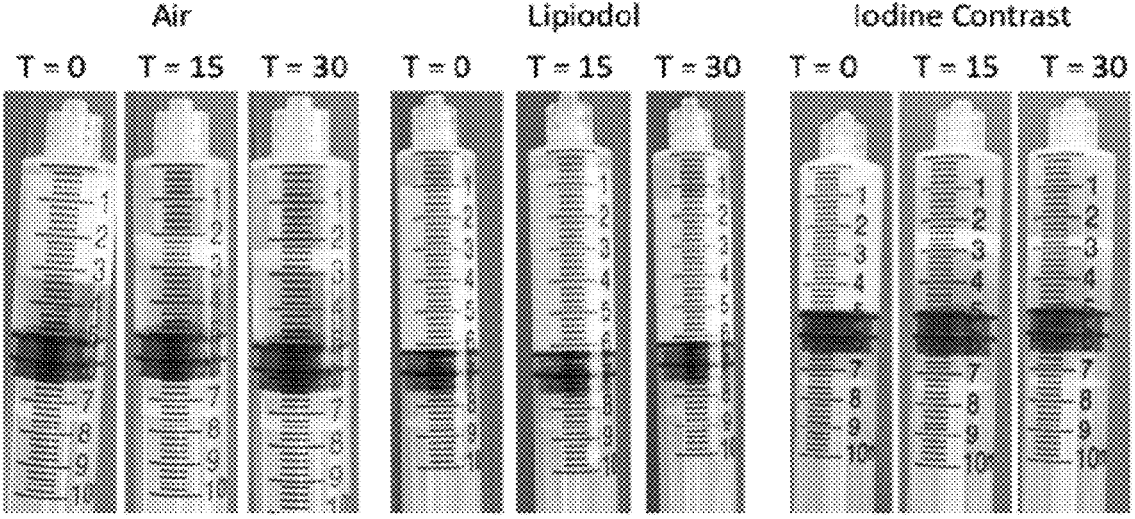
FIG. 5(A-C) illustrate: (A) Representative images of the trials with air only, and with addition of LIPIODOL or iodine contrast at different timepoints; (B) Percentage of foam decay for a different formulation; and (C) Decay curves for all formulation and different STS:gas ratios.
Figures 5B, 5C:
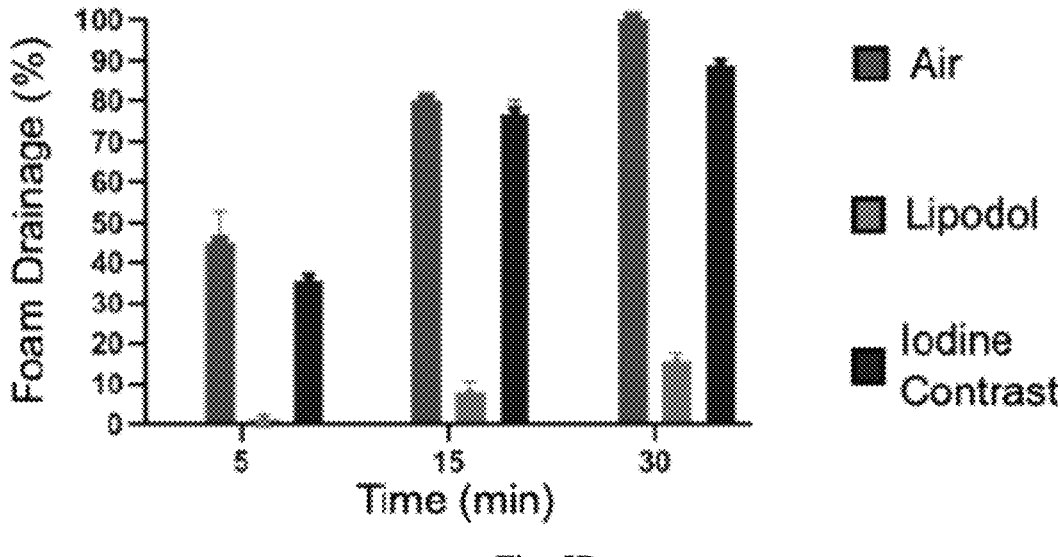

FIGS. 5(A-C) show that foam stability was significantly influenced by LIPIODOL and iodine contrast. When LIPIODOL was combined with the air mixture, there was a 35-44% increase in foam stability for the 1:4 air to STS and 1:4 air to STS at 5 minutes, respectively. At 10 minutes, there was an average of 74% increase in foam remaining compared to foam made without contrast. We observed total foam decay in the air mixture at 30 minutes, while the LIPIODOL mix had 84% foam remaining in the 1:1.5 and 47% foam remaining for the 1:4 ratio. Iodine contrast had a similar effect, but smaller in magnitude. At the 30 minutes mark, iodine contrast had 5 to 11% remaining for the 1:1.5 and 1:4 ratios, respectively. The trend continued at the 45 minute mark.

The introduction of LIPIODOL highly increases the sclerosing foam stability whereas iodine contrast had similar but milder effect. These suggest that iodine contrast can be used to enhance contrast of sclerosing foam without changing the properties whereas LIPIODOL can provide contrast and enhance stability.

Example 2

Optimizing Sclerosing Foam Stability: An Evaluation of Gas Formulation Parameters The lifetime of the sclerosing foam is typically less than 10 minutes When made with room air, as per standard protocol. In some circumstances, a longer lasting sclerosing foam may be required. In this Example, we evaluated the impact of air to foam material ratio and to examine the inclusion of alternative high molecular weight, hydrophobic perfluorocarbon gasses on the stability of clinically utilized sclerosing foam (SOTRADECOL). We also studied the impact of total foam volume on the decay rate.

Materials and Methods

Foams were generated using two 10 mL syringes connected by a 3-way stopcock. One syringe was filled with gas (either room air, $C_3F_8$, or $C_4F_{10}$ high MW perfluorocarbons (PFC)), the other contained 2 mL of sodium tetradecyl-sulfate (STS). The components were mixed through the stopcock 30 times (Tessari's method). Consistent temperature and pressure were assured throughout all experiments. Each trial set encompassed ratios of 1:1.5, 2, 3, and 4 mL of STS to gas. Foam decay (% change from the initial foam volume) was monitored using a 4K camera over 1 hour, followed by hourly snapshots for 3 hours. Supplementary images were captured at the 24-hour mark if any foam persisted. All trials were repeated 3 times for variability assessment.

Results

FIG. 3 shows images of foams produced at an STS:air ratio of 1:4 and STS:$C_3F_8$ ratio of 1:4 upon production and after 5 minutes and 30 minutes, respectively. The size difference between bubbles of standard foams formed using STS:air and those formed with $C_3F_8$ was substantially different with foams produced using STS:air having an average bubble diameter of about 200 μm to about 500 μm versus foams produced using STS:$C_3F_8$ having an average bubble diameter of about 10 μm to about 100 μm. The bubbles for the $C_3F_8$ foams were also much more stable remaining consistently smaller than 200 μm after 30 minutes; whereas regular foams had mm sized bubbles at 5 minutes.

Figure 4A:
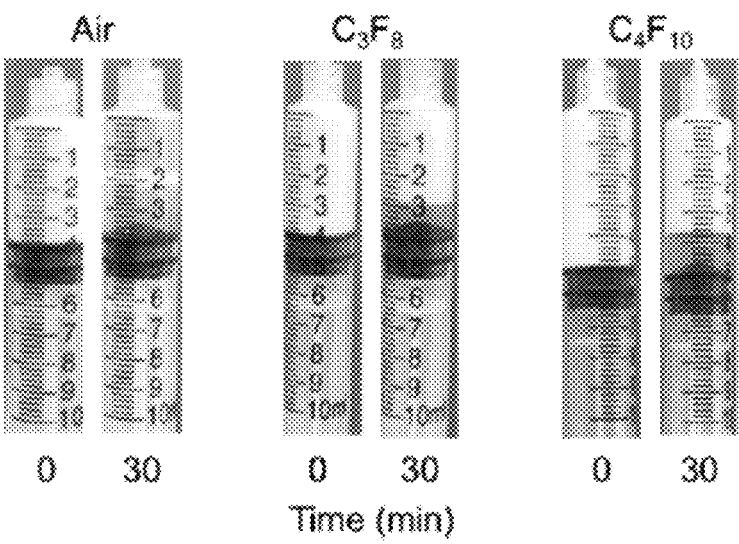
FIGS. 4(A-C) illustrate: (A) Representative images of the trials with different gasses; (B) Percentage of foam decay for different gasses; and (C) Decay curves for all gases and different STS:air ratios.
Figure 4B:
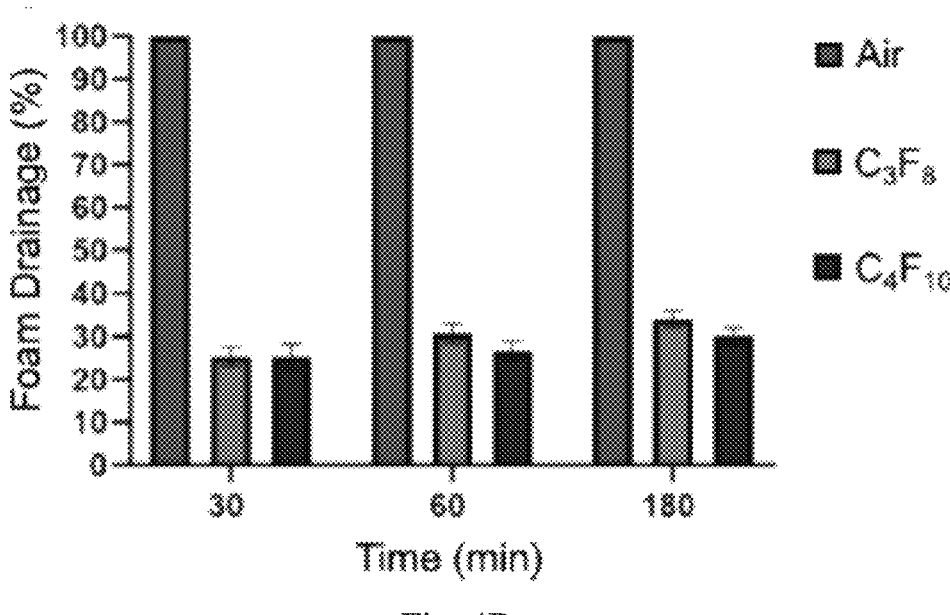
Figure 4C:
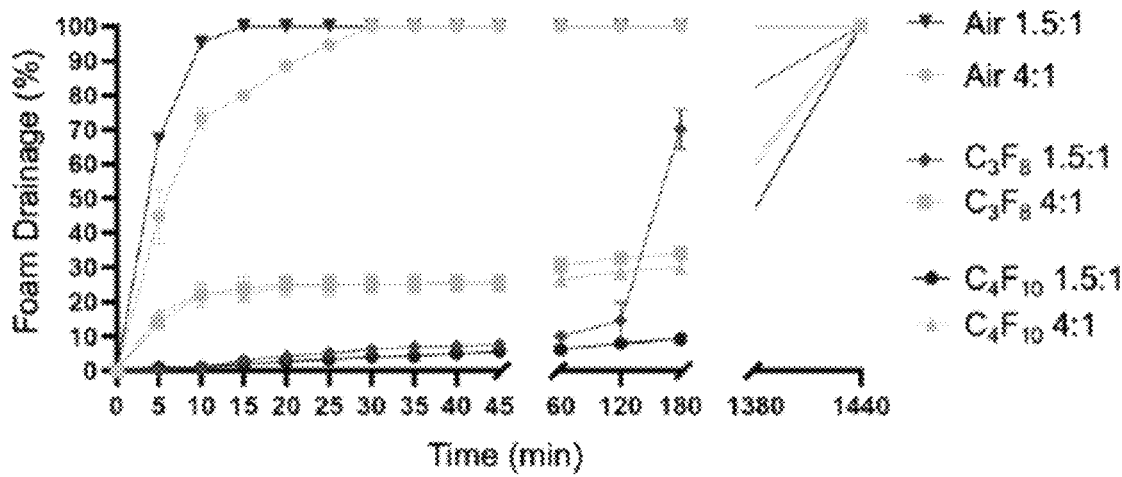

FIG. 4(A-C) illustrate that foams produced using perfluorocarbon gases resulted in a foams with a significant increase in foam stability compared to air. When air was used, we observed 100% foam decay within 30 minutes, while $C_3F_8$ and $C_4F_{10}$ showed 25% decay. $C_4F_{10}$ demonstrated overall better stability at the 1, 2, and 3 hour marks compared to $C_3F_8$. $C_4F_{10}$ experienced 30% decay after 3 hours, while $C_3F_8$ reached 34% decay within the same timeframe. To assess the effect of total volume on foam decay, trials with constant foam volumes (4 mL) but varied gas:STS ratios were conducted. $C_3F_8$ showed 32% and 76% decay for the 1:1.5 and 1:4 ratios respectively at the 3 hour point. In the constant volume trials with $C_4F_{10}$, 1:1.5 reached 78% decay, and 1:4 reached 68% at the 3 hour point, indicating volume's influence on decay. This pattern was consistent in trials with 1:2 and 1:3 gas to foam ratios as well. Similar trends were observed in air trials, where regular air reached 100% decay after 20 minutes for all ratios, while the same volume trials reached 100% decay at 30 minutes for 1:1.5 and 15 minutes for 1:4.

$C_3F_8$ and $C_4F_{10}$ greatly increase the stability with STS foam compared to air, and $C_4F_{10}$ exhibited better stability over time than $C_3F_8$.

Example 3

This Example describes how the inclusion of iodinated contrast media and alternative high molecular weight, hydrophobic perfluorocarbon gasses influence the stability of clinically utilized sclerosing foam (SOTRADECOL). We also studied the impact of total foam volume on the decay rate.

Materials and Methods

Foams were generated using two 10 mL syringes connected by a 3-way stopcock. One syringe was filled with either room air, $C_3F_8$, or $C_4F_{10}$ high MW perfluorocarbons (PFC), while the other contained 2 mL of sodium tetradecyl-sulfate (STS). The components were mixed through the stopcock 30 times (Tessari's method). For contrast-bearing formulations, 1 mL of LIPIODOL (Guerbet, Villepinte, France) or OMNIPAQUE (Marlborough, United States) were added to the mixture (2 mL of STS+1 mL of contrast). Each trial set encompassed ratios of 1:1.5, 2, 3, and 4 mL of STS to room air. Foam decay was monitored using a 4K camera over 1 hour, followed by hourly snapshots for 3 hours. Supplementary images were captured at the 24-hour mark if any foam persisted. Decay of foam was calculated using the formula (foam left in syringe)/(total volume).

Figure 6A:
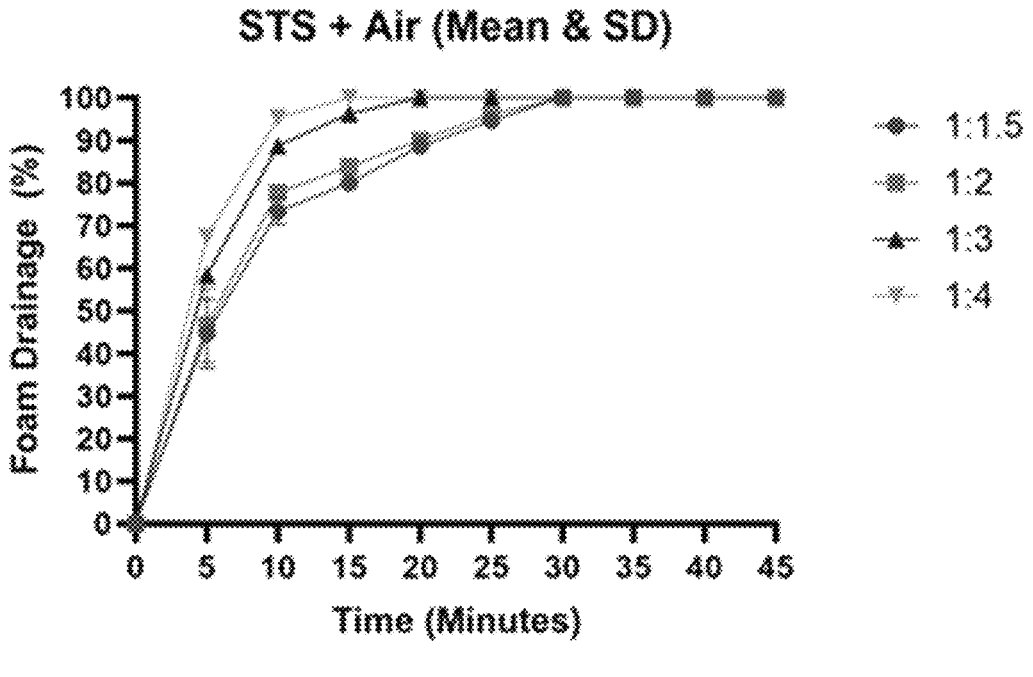
FIGS. 6(A-B) illustrate plots showing percentage of foam decay for formulations of (A) STS:air at different ratios; and (B) STS:air with LIPIODOL at different ratios.
Figure 6B:
Figure 6B:
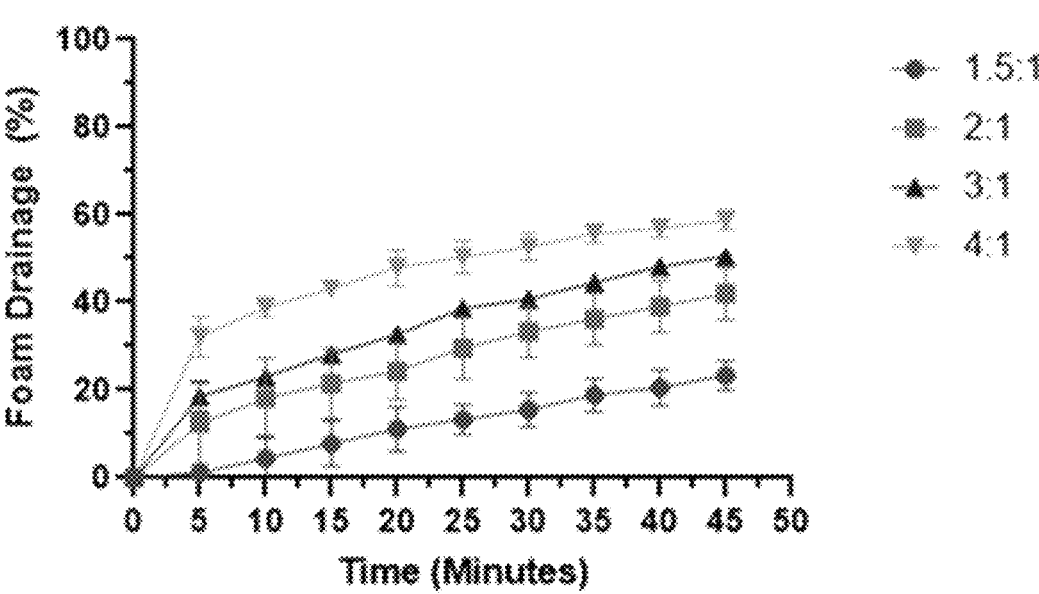

FIGS. 6(A-B) illustrate plots showing percentage of foam decay for formulations of (A) STS:air at different ratios and (B) STS:air with LIPIODOL at different ratios.

Figure 7A:
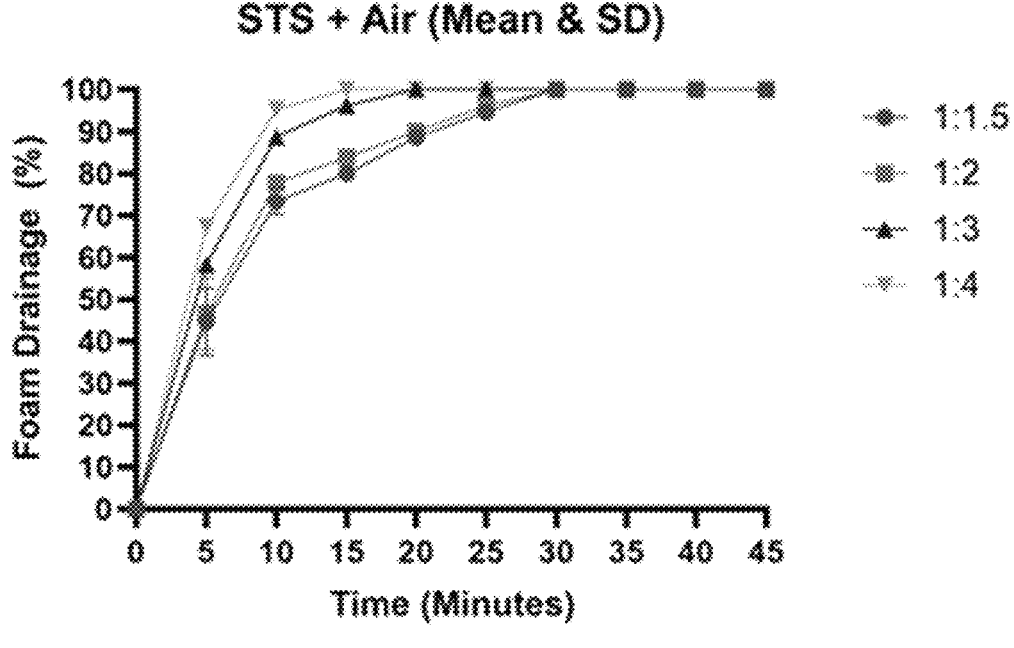
FIGS. 7(A-B) illustrate plots showing percentage of foam decay for formulations of (A) STS:air at different ratios; and (B) STS:air with iodine contrast at different ratios.
Figure 7B:
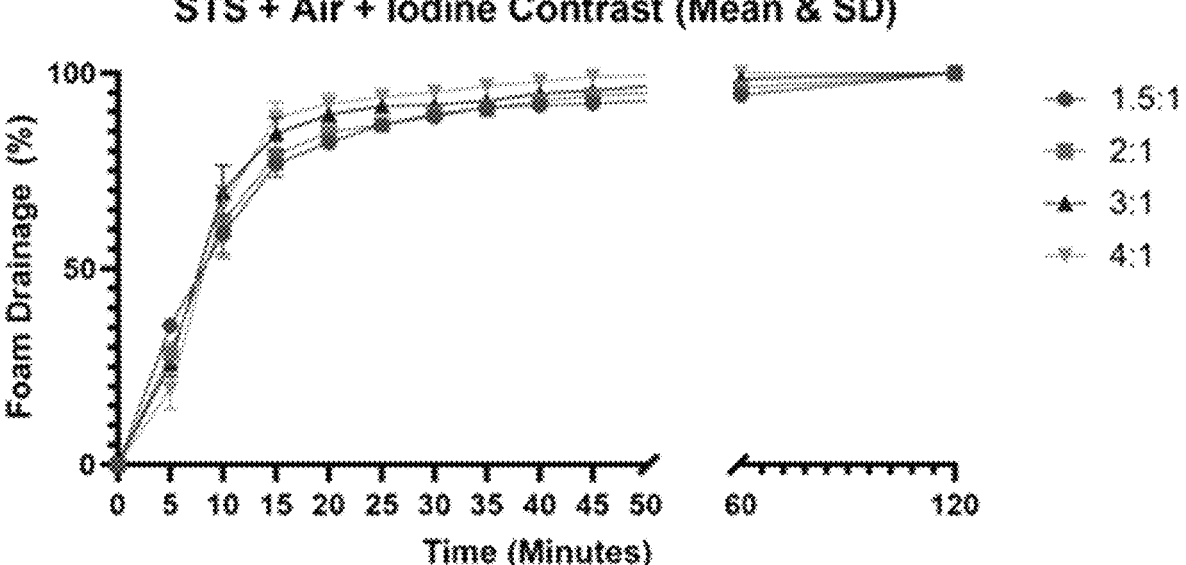

FIGS. 7(A-B) illustrate plots showing percentage of foam decay for formulations of (A) STS:air at different ratios and (B) STS:air with iodine contrast at different ratios.

Figure 8:
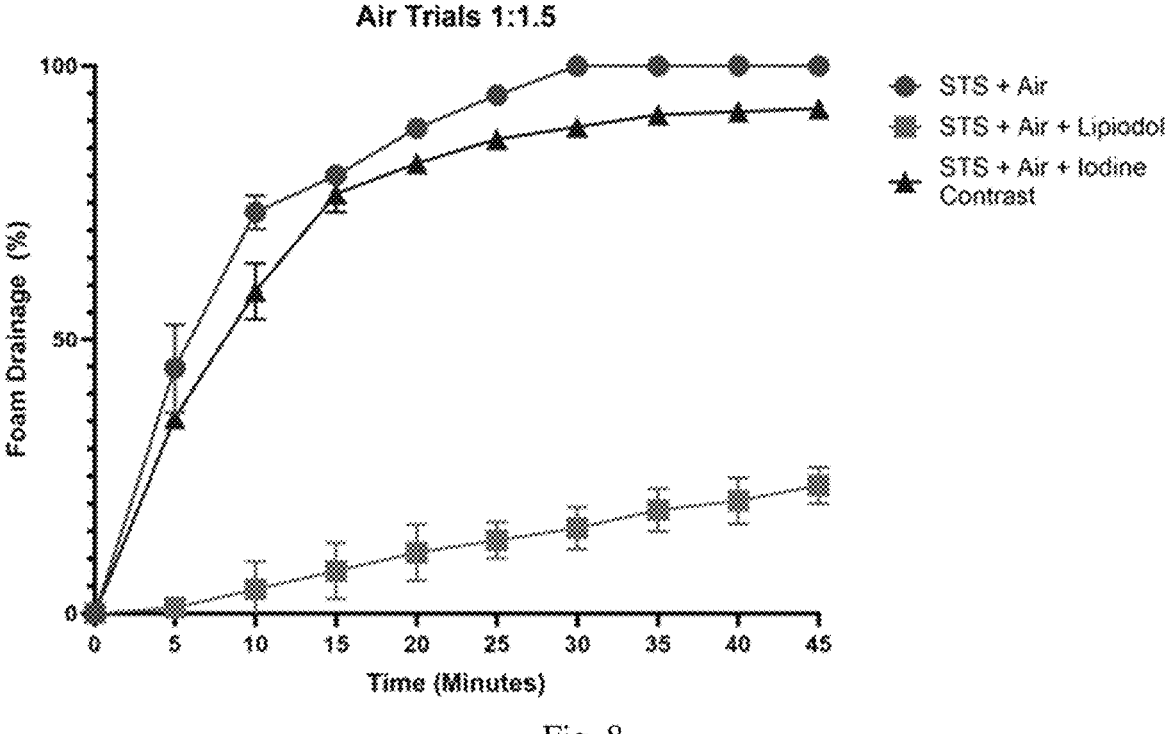
FIG. 8 illustrates plots showing percentage of foam decay for formulations of STS:air, STS:air with LIPIODOL, or STS:air with iodine contrast at STS:air ratio of 1:1.5.

FIG. 8 illustrates plots showing percentage of foam decay for formulations of STS:air, STS:air with LIPIODOL, or STS:air with iodine contrast at STS:air ratio of 1:1.5.

Figure 9:
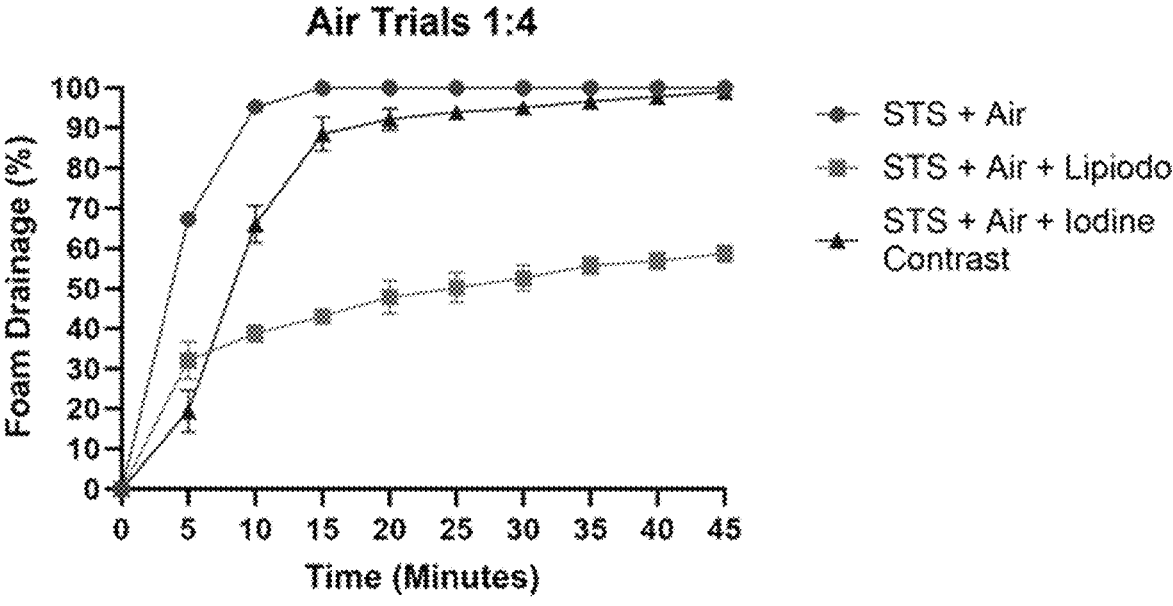
FIG. 9 illustrates plots showing percentage of foam decay for formulations of STS:air, STS:air with LIPIODOL, or STS:air with iodine contrast at STS:air ratio of 1:4.

FIG. 9 illustrates plots showing percentage of foam decay for formulations of STS:air, STS:air with LIPIODOL, or STS:air with iodine contrast at STS:air ratio of 1:4.

Figure 10:
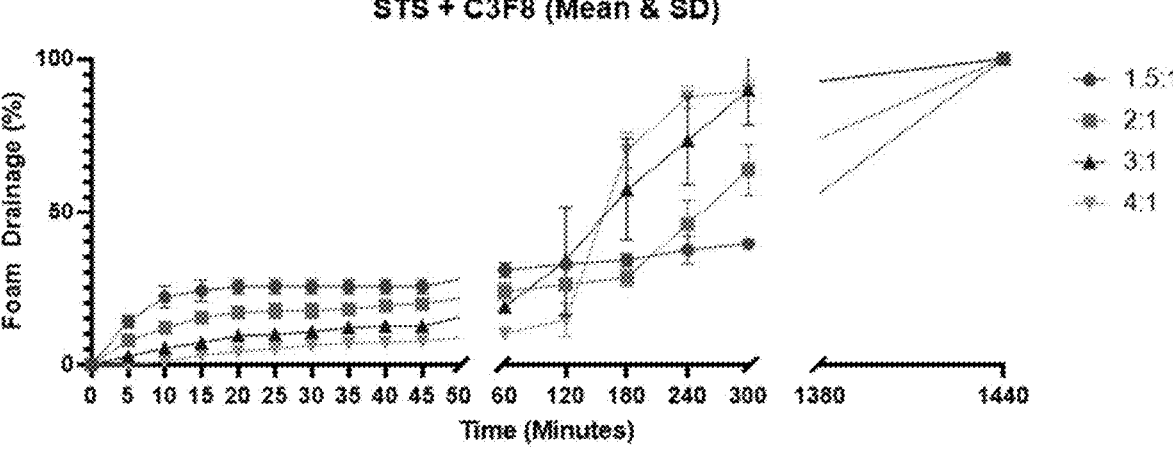
FIG. 10 illustrates plots showing percentage of foam decay for formulations of $STS:C_3F_8$ at different ratios.

FIG. 10 illustrates plots showing percentage of foam decay for formulations of STS:$C_3F_8$ at different ratios.

Figure 11:
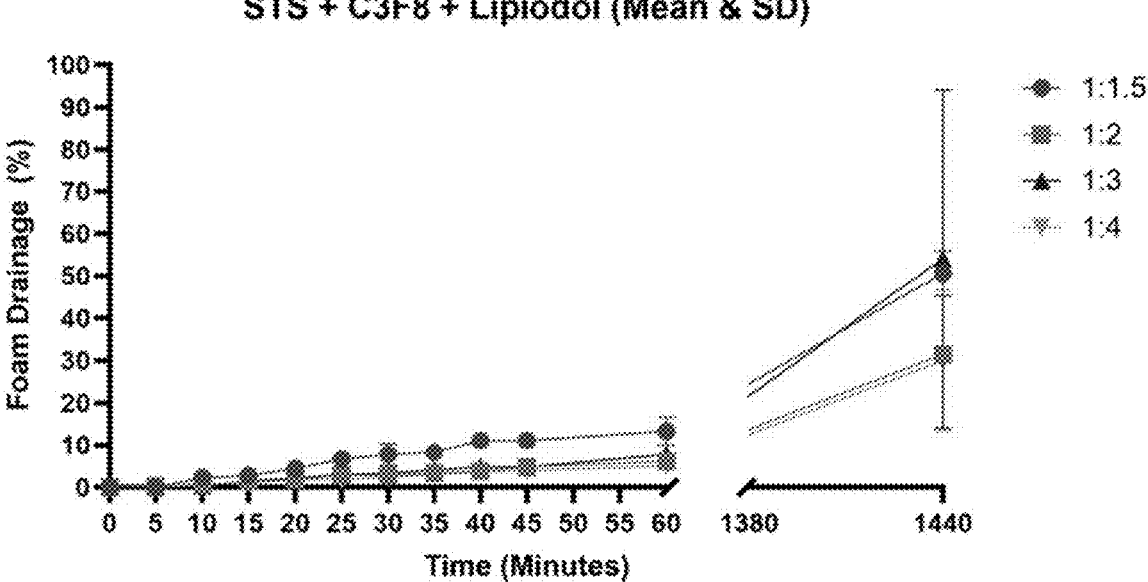
FIG. 11 illustrates plots showing percentage of foam decay for formulations of $STS:C_3F_8$ with LIPIODOL at different ratios.

FIG. 11 illustrates plots showing percentage of foam decay for formulations of STS:$C_3F_8$ with LIPIODOL at different ratios.

Figure 12:
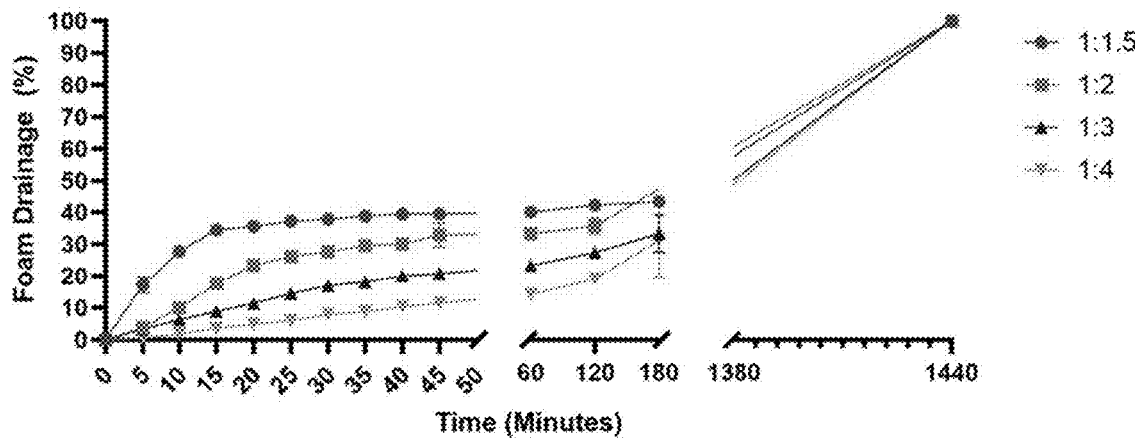
FIG. 12 illustrates plots showing percentage of foam decay for formulations of $STS:C_3F_8$ with iodine contrast at different ratios.

FIG. 12 illustrates plots showing percentage of foam decay for formulations of STS:$C_3F_8$ with iodine contrast at different ratios.

Figure 13:
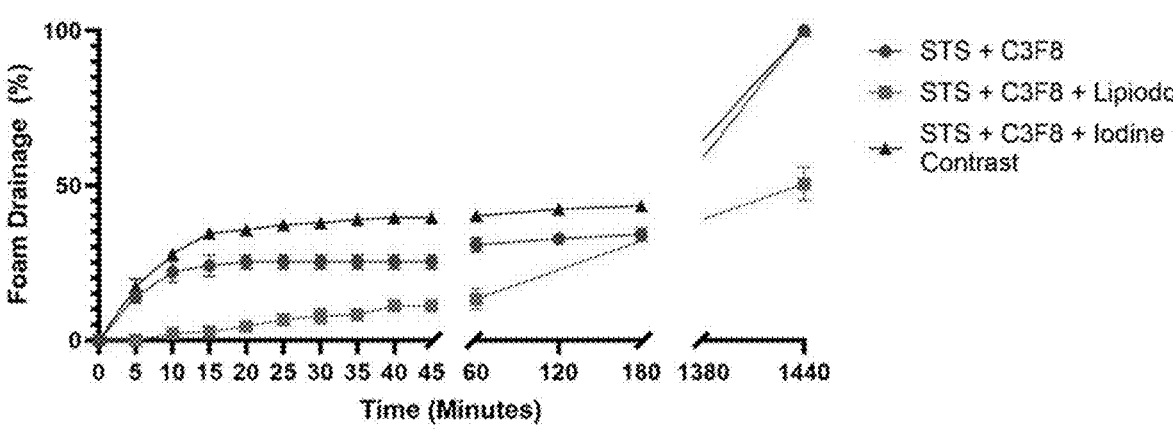
FIG. 13 illustrates plots showing percentage of foam decay for formulations of $STS:C_3F_8$, $STS:C_3F_8$ with LIPIODOL, or $STS:C_3F_8$ with iodine contrast at $STS:C_3F_8$ ratio of 1:1.5.

FIG. 13 illustrates plots showing percentage of foam decay for formulations of STS:$C_3F_8$, STS:$C_3F_8$ with LIPIODOL, or STS:$C_3F_8$ with iodine contrast at STS:$C_3F_8$ ratio of 1:1.5.

Figure 14:
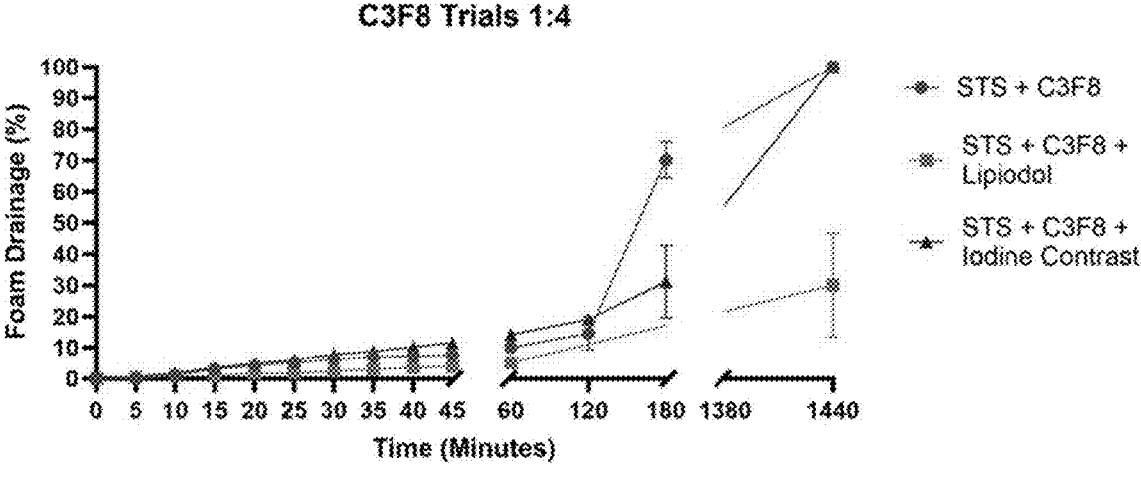
FIG. 14 illustrates plots showing percentage of foam decay for formulations of $STS:C_3F_8$, $STS:C_3F_8$ with LIPIODOL, or $STS:C_3F_8$ with iodine contrast at $STS:C_3F_8$ ratio of 1:4.

FIG. 14 illustrates plots showing percentage of foam decay for formulations of STS:$C_3F_8$, STS:$C_3F_8$ with LIPIODOL, or STS:$C_3F_8$ with iodine contrast at STS:$C_3F_8$ ratio of 1:4.

Figure 15:
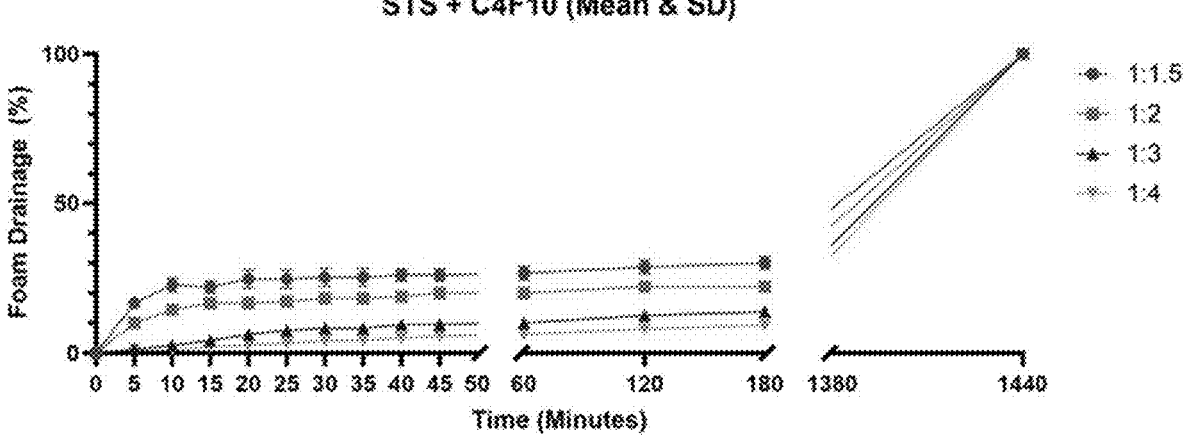
FIG. 15 illustrates plots showing percentage of foam decay for formulations of $STS:C_4F_{10}$ at different ratios.

FIG. 15 illustrates plots showing percentage of foam decay for formulations of STS:$C_4F_{10}$ at different ratios.

Figure 16:
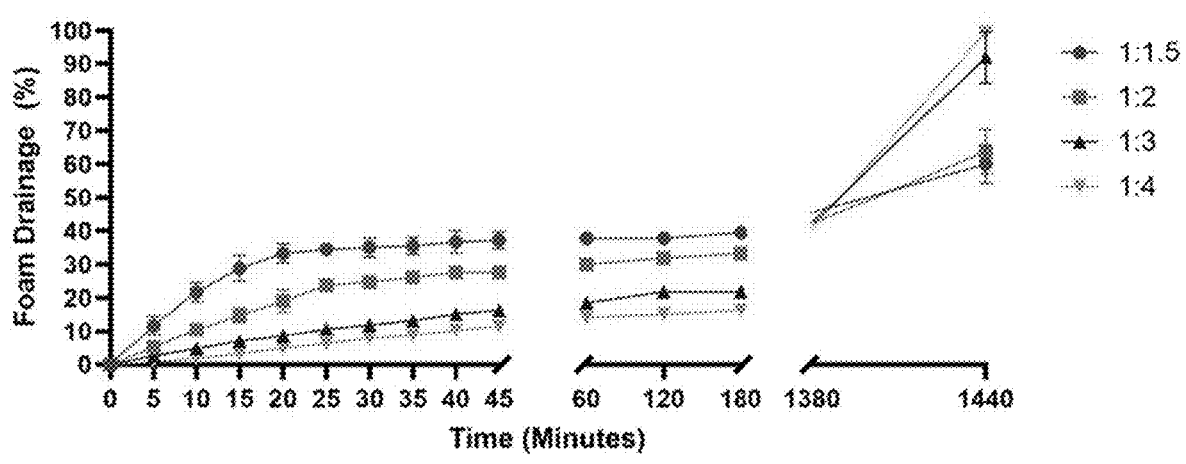
FIG. 16 illustrates plots showing percentage of foam decay for formulations of $STS:C_4F_{10}$ with iodine contrast at different ratios.

FIG. 16 illustrates plots showing percentage of foam decay for formulations of STS:$C_4F_{10}$ with iodine contrast at different ratios.

Figure 17:
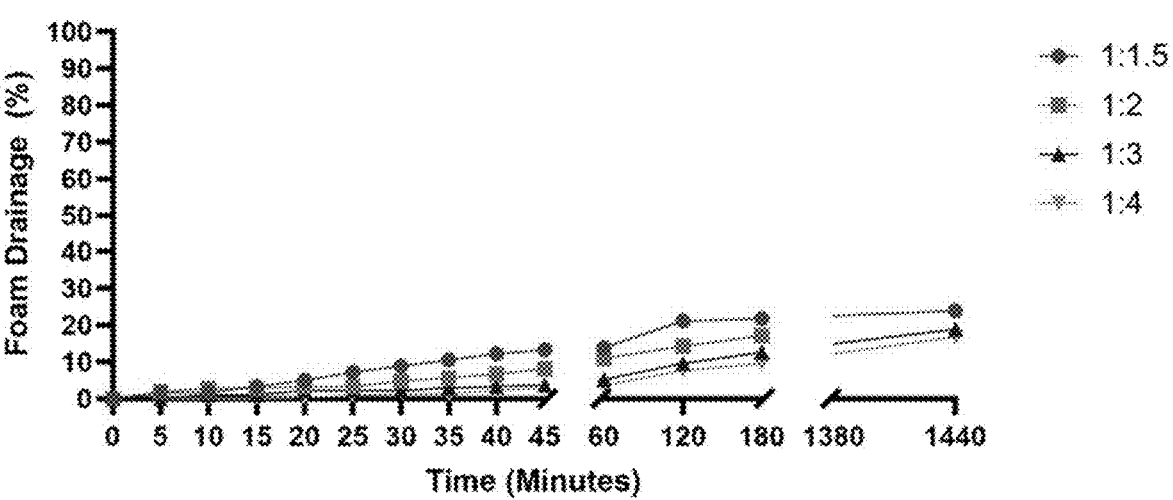
FIG. 17 illustrates plots showing percentage of foam decay for formulations of $STS:C_4F_{10}$ with LIPIODOL at different ratios.

FIG. 17 illustrates plots showing percentage of foam decay for formulations of STS:$C_4F_{10}$ with LIPIODOL at different ratios.

Figure 18:
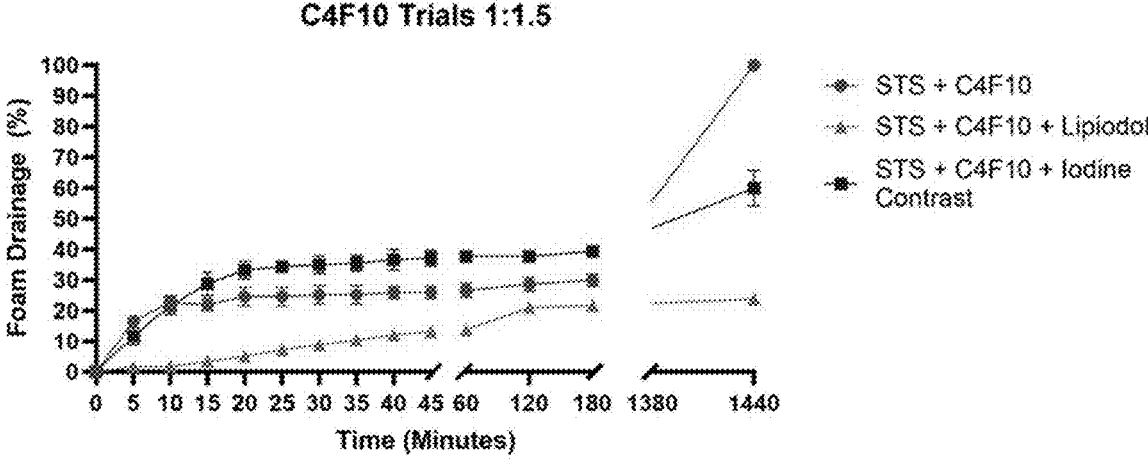
FIG. 18 illustrates plots showing percentage of foam decay for formulations of $STS:C_4F_{10}$, $STS:C_4F_{10}$ with LIPIODOL, or $STS:C_4F10_8$ with iodine contrast at $STS:C_4F_{10}$ ratio of 1:1.5.

FIG. 18 illustrates plots showing percentage of foam decay for formulations of STS:$C_4F_{10}$, STS:$C_4F_{10}$ with LIPIODOL, or STS:$C_4F10_8$ with iodine contrast at STS:$C_4F_{10}$ ratio of 1:1.5.

Figure 19:
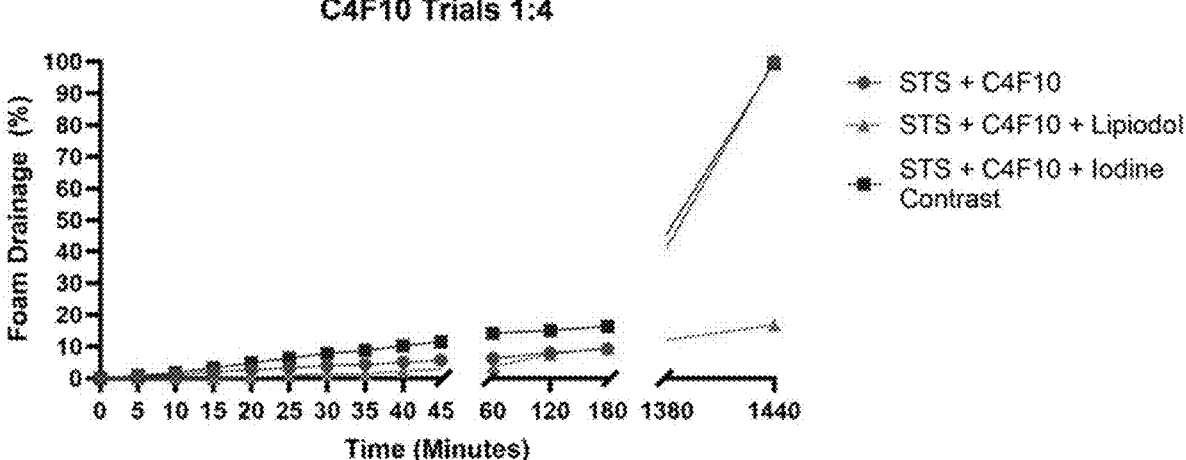
FIG. 19 illustrates plots showing percentage of foam decay for formulations of $STS:C_3F_8$, $STS:C_4F_{10}$ with LIPIODOL, or $STS:C_4F_{10}$ with iodine contrast at $STS:C_4F_{10}$ ratio of 1:4.

FIG. 19 illustrates plots showing percentage of foam decay for formulations of STS:$C_3F_8$, STS:$C_4F_{10}$ with LIPIODOL, or STS:$C_4F_{10}$ with iodine contrast at STS:$C_4F_{10}$ ratio of 1:4.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A sclerosing foam comprising:

a liquid phase and a gas phase, wherein the liquid phase comprises at least one sclerosing agent and the gas phase comprises at least about 50% by volume of a perfluorocarbon gas.

2. The sclerosing foam of claim 1, wherein the gas phase comprises at least about 75% by volume $C_2F_6$, $C_3F_8$, and/or $C_4F_{10}$.

3. The sclerosing foam of claim 1, wherein the gas phase comprises at least about 90% by volume $C_2F_6$, $C_3F_8$, and/or $C_4F_{10}$.

4. The sclerosing foam of claim 1, wherein the sclerosing agent includes a solution of an anionic surfactant.

5. The sclerosing foam of claim 1, wherein the liquid phase includes sodium tetradecyl sulfate or an analogue thereof in an aqueous carrier.

6. The sclerosing foam of claim 1, wherein the liquid phase includes about 0.3% w/v to about 3% w/v of sodium tetradecyl sulfate in an aqueous carrier.

7. The sclerosing foam of claim 1, wherein the foam has liquid to gas ratio of the foam is 1:1.5 to 1:4.

8. The sclerosing foam of claim 1, further comprising at least one of radio-opaque contrast agent in an amount effective to enhance contrast and/or stability of the foam.

9. The sclerosing foam of claim 8, wherein the radio-opaque contrast agent includes an ethiodized oil contrast agent.

10. The sclerosing foam of claim 9, wherein the ethiodized oil contrast agent includes a combination of iodine and ethyl esters of fatty acids of poppyseed oil.

11. The sclerosing foam of claim 1, further comprising an antibiotic.

12. The sclerosing foam of claim 1, having a half-life of at least about 10 minutes.

13. The sclerosing foam of claim 1, wherein at least about 75%, at least about of bubbles of the foam have a diameter less than about 200 μm upon production and have a diameter that remains consistently smaller than about 200 μm after about 30 minutes.

14. A sclerosing foam comprising:

a liquid phase and a gas phase, wherein the liquid phase comprises at least one sclerosing agent and optionally at least one radio-opaque contrast agent and the gas phase comprises at about 75% by volume $C_2F_6$, $C_3F_8$, and/or $C_4F_{10}$, wherein at least about 75%, at least about of bubbles of the foam have a diameter less than about 200 μm upon production and have a diameter that remains consistently smaller than about 200 μm after about 30 minutes.

15. The sclerosing foam of claim 14, wherein the gas phase comprises at least about 90% by volume $C_2F_6$, $C_3F_8$, and/or $C_4F_{10}$.

16. The sclerosing foam of claim 14, wherein the sclerosing agent is an aqueous solution of anionic surfactant.

17. The sclerosing foam of claim 14, wherein the liquid phase includes sodium tetradecyl sulfate or an analogue thereof.

18. The sclerosing foam of claim 14, wherein the liquid phase includes about 0.3% w/v to about 3% w/v of sodium tetradecyl sulfate in an aqueous carrier.

19. The sclerosing foam of claim 14, wherein the foam has liquid to gas ratio of the foam is 1:1.5 to 1:4.

20. The sclerosing foam of claim 14, having a half-life of at least about 60 minutes.

* * * * *